United States Patent
Di Pierro

(10) Patent No.: US 7,354,610 B2
(45) Date of Patent: Apr. 8, 2008

(54) PHARMACEUTICAL AND COSMETIC COMPOSITION AGAINST SKIN AGING

(75) Inventor: Francesco Di Pierro, Milan (IT)

(73) Assignee: Indena S.p.A., Milan (IT)

(*) Notice: Subject to any disclaimer, the term of this patent is extended or adjusted under 35 U.S.C. 154(b) by 0 days.

(21) Appl. No.: 11/783,331

(22) Filed: Apr. 9, 2007

(65) Prior Publication Data

US 2007/0184134 A1    Aug. 9, 2007

Related U.S. Application Data

(62) Division of application No. 10/477,703, filed as application No. PCT/EP02/05147 on May 10, 2002, now Pat. No. 7,214,395.

(30) Foreign Application Priority Data

May 17, 2001   (IT)  ............. MI2001A1022

(51) Int. Cl.
 *A61K 36/87* (2006.01)
 *A61K 36/00* (2006.01)

(52) U.S. Cl. .................. 424/766; 424/725
(58) Field of Classification Search .......... None
See application file for complete search history.

(56) References Cited

U.S. PATENT DOCUMENTS 4,963,527 A * 10/1990 Bombardelli et al. ......... 514/25
5,554,647 A    9/1996 Perricone

FOREIGN PATENT DOCUMENTS

| EP | 0 275 224 | 7/1988 |
|---|---|---|
| EP | 0 283 713 | 9/1988 |
| EP | 0 659 755 | 6/1995 |
| WO | WO 00/40215 | 7/2000 |
| WO | WO 01/78674 | 10/2001 |

* cited by examiner

*Primary Examiner*—Patricia Leith
(74) *Attorney, Agent, or Firm*—Young & Thompson

(57) ABSTRACT

Pharmaceutical and cosmetic compositions for the prevention of skin aging, containing phospholipid complexes of extracts of *Vitis vinifera*, and phospholipid complexes of standardized extract from *Centella asiatica*.

10 Claims, No Drawings

PHARMACEUTICAL AND COSMETIC COMPOSITION AGAINST SKIN AGING

FIELD OF THE INVENTION

The present invention relates to pharmaceutical and cosmetic compositions against the skin aging containing ingredients of vegetable origin.

More particularly, the present invention relates to pharmaceutical and cosmetic compositions for the prevention of skin aging, containing phospholipid complexes of extracts of *Vitis vinifera*, and phospholipid complexes of triterpenes extracted from *Centella asiatica*.

BACKGROUND OF THE INVENTION

Skin aging is a complex biological process affecting various layers of the skin, but whose major effects are seen in the dermis. There are two biologically independent aging processes that occur simultaneously. The first is intrinsic aging, which affects skin as well as, most likely, the internal organs. The second is extrinsic aging or photo-aging which is the result of exposure to the elements, primarily ultraviolet irradiation. The consequences of innate aging can be observed all over the skin, including areas protected from the sun. In the areas exposed to the sun, particularly the face and the backs of the hands, photoaging damage is superimposed to tissue degeneration due to innate aging. Thus, the most noticeable changes on facial and neck skin, the primary areas that patients are concerned about, result from the combination of intrinsic and extrinsic aging processes. It has been suggested that as much as 80% of facial aging may be ascribed to exposure to the sun, although other factors (i.e. cigarette smoking) can contribute to premature wrinkling.

From a biochemical standpoint, photoaging is thought to be induced mainly by: some proteases, mainly metalloproteases, which are overproduced and overrealesed by keratinocytes and fibroblasts as a consequence of the interaction with ultraviolet radiation (these proteases are degradative enzymes irreversibly damaging collagen, elastin and hyaluronic acid, bringing about dermis scars and visible wrinkles); and by oxidative stress, able to eliminate the normal skin antioxidant defenses in a very short time.

OBJECT OF THE INVENTION

On the basis of these general considerations, it is clear the need to protect the skin from premature aging by a tool able to counteract the action of the proteases on the dermis (while increasing the capability of fibroblasts to produce and release new collagen fibers) and the disappearance of the antioxidant defenses from the skin.

SUMMARY OF THE INVENTION

The present invention fulfills this need to protect the skin from premature aging, by providing pharmaceutical and cosmetic compositions containing the following ingredients of vegetable origin:
a) phospholipid complexes of standardized extract 0.1-2.5% of *Vitis vinifera*,
b) phospholipid complexes of standardized extract 0.1-2.5% of *Centella asiatica*.

More preferably, the pharmaceutical and cosmetic compositions of the present invention contain the following ingredients of vegetable origin in the following percentages:

a) phospholipid complexes of standardized extract 1% of *Vitis vinifera*,
b) phospholipid complexes of standardized extract 1% of *Centella asiatica*.

The phospholipid complexes of standardized extract of *Vitis vinifera* (also referred to as "components a") are disclosed in EP 275,224. Said extracts consist of the polyphenolic fraction contained in *Vitis vinifera* seeds, and comprise gallic acid, monomers, dimers, trimers, tetramers, pentamers, examers and heptameters of catechin and epicatechin free and esterified with gallic acid.

In vitro and in vivo studies have evidenced the high antioxidizing activity of said extracts (10 to 200 times as much that of vitamin E, depending on the experimental model), which includes the scavenging of the most reactive radical species, and counteracts all the phenomena related to the activity of free radicals. Said extract is further characterized by the capability to inhibit xanthine-oxidase and to chelate $Cu^{++}$ and $Fe^{+++}$, thus preventing the enzymatic release of free radicals in tissues. Finally, the extract of *Vitis vinifera* inhibits collagenase and other proteases, thereby protecting the connective tissue and the skin from the harmful action of proteolytic enzymes released following UV irradiation and during the development of an inflammatory skin response, and it has selective affinity to the skin and the circulatory structures, such as microvessels and capillaries, thereby also protecting the microcirculatory district.

The phospholipid complexes of standardized extract of *Centella asiatica* (also referred to as "components b") are disclosed in EP 283,713.

This extract consists of a 4:3:3 mixture of three different molecules having strong activity on collagen metabolism: asiaticoside, asiatic acid and madecassic acid. These molecules improve the capability of the fibroblasts to up-take amino acids such as L-Proline and L-Hydroxyproline that, from a quali-quantitative standpoint, are the most important amino acids in the collagen formula. An improved synthesis of collagen means a faster substitution of the degraded old fibers of collagen with the new ones.

Components a) and b), when tested toxicologically, showed. neither toxic nor irritative actions towards the treated tissues.

The compositions of the present invention may optionally contain, in addition to components a) and b) indicated above, also other active ingredients such as vitamin E (0.2-1%), zinc (0.1-0.3%), hydroxyacids (0.1-1%) and glycyrrhetinic acid or a complex thereof with phospholipids (0.1-2.5%), to improve the antioxidant, anti-aging and anti-nflammatory properties of the composition.

The compositions of the present invention will be administered topically, in the form of suitable formulations liquid (such as gel, lotions, milks, emulsions, foams and the like) or solid or semi-solid (such as creams, ointments, lipsticks, and the like). Said formulations will be prepared according to conventional methods, such as those described in "Remington's Pharmaceutical Handbook", Mack Publishing Co., NY, USA, together with suitable excipients, such as emollients, moisturizers, thickening agents, emulsifiers, dyes, flavors and the like.

Some examples of compositions according to the invention are reported in the following.

EXAMPLE 1

Oil-in-Water Emulsion

| 100 g contain: | |
|---|---|
| Phospholipid complexes of extract of *Vitis vinifera* | 0.20 g |
| Phospholipid complexes of triterpenes extracted from *Centella asiatica* | 1.00 g |
| Isostearyl isostearate (Gattefossé) | 2.50 g |
| Polyisoprene (Syntesqual - Vevy) | 2.50 g |
| Decyl oleate (Cetiol V - Henkel) | 2.00 g |
| Cetyl palmitate (Cutina CP - Henkel) | 2.00 g |
| Cetearyl Isononanoate (Cetiol SN - Henkel) | 2.00 g |
| Polysorbate 80 (Tween 80 - ICI) | 1.00 g |
| Imidazolidinyl urea | 0.30 g |
| Tocoferol | 0.20 g |
| Ascorbyl Palmitate | 0.10 g |
| Methyl chloroisothiazolinone (e) Methyl isothiazolinone (Kathon CG-Rohm & Haas) | 0.05 g |
| Disodium EDTA | 0.10 g |
| Butylated hydroxytoluene | 0.05 g |
| Polyacrylamide (e) $C_{13-14}$ Isoparaffin (e) Laureth-7 (Spiegel 305 - Seppic) | 2.50 g |
| Perfume | 0.10 g |
| Purified water q.s. to | 100.0 g |

EXAMPLE 2

Oil-in-Water Emulsion

| 100 g contain: | |
|---|---|
| Phospholipid complexes of extract of *Vitis vinifera* | 0.50 g |
| Phospholipid complexes of triterpenes extracted from *Centella asiatica* | 0.50 g |
| Phospholipid complexes of glycyrrhetinic acid | 1.50 g |
| $C_{12-15}$ Alkyl benzoate (Finsolv TN - Finetex) | 4.00 g |
| Cetyl palmitate (Cutina CP - Henkel) | 3.00 g |
| Polyisoprene (Syntesqual - Vevy) | 2.50 g |
| Isostearyl isostearate (Gaffefossé) | 2.50 g |
| Polysorbate 80 (Tween 80 - ICI) | 1.00 g |
| Imidazolidinyl urea | 0.30 g |
| Methyl chloroisothiazolinone (e) Methyl isothiazolinone (Kathon CG-Rohm & Haas) | 0.05 g |
| Tocoferol | 0.20 g |
| Ascorbyl Palmitate | 0.10 g |
| Disodium EDTA | 0.10 g |
| Citric acid | 0.05 g |
| Polyacrylamide (e) $C_{13-14}$ Isoparaffin (e) Laureth-7 (Spiegel 305 - Seppic) | 2.00 g |
| Butylated hydroxytoluene | 0.05 g |
| Perfume | 0.10 g |
| Purified water q.s. to | 100.0 g |

The invention claimed is:

1. A composition comprising:
   phospholipid complexes of standardized extract of *Vitis vinifera*; and
   phospholipid complexes of standardized extract of *Centella asiatica* and
   wherein said extracts are of vegetable origin.

2. The composition according to claim 1, further comprising at least one additional active ingredient selected from the group consisting of vitamin E, zinc, hydroxyacids, glycyrrhetinic acid and a complex of glycyrrhetinic acid with phospholipids.

3. The composition according to claim 1, further comprising at least one carrier or excipient selected from the group consisting of emollients, moisturizers, thickening agents, emulsifiers, dyes, and flavors.

4. The composition according to claim 1, wherein said composition is a cosmetic composition for retarding noticeable effects of skin aging.

5. The composition according to claim 1, wherein
   said phospholipid complexes of standardized extract of *Vitis vinifera* are present in an amount of 0.1-2.5% of said composition, and
   said phospholipid complexes of standardized extract of *Centella asiatica* are present in an amount of 0.1-2.5% of said composition.

6. A composition comprising:
   0.1-2.5% phospholipid complexes of standardized extract of *Vitis vinifera*;
   0.1-2.5% phospholipid complexes of standardized Extract of *Centella asiatica*;
   a carrier or an excipient,
   wherein said extracts are of vegetable origin, and
   said composition does not contain fish cartilage extract.

7. The composition of claim 6, wherein said carrier or excipient is selected from the group consisting of emollients, moisturizers, thickening agents, emulsifiers, dyes, flavors and mixtures thereof.

8. The composition according to claim 6, further comprising at least one additional active ingredient selected from the group consisting of vitamin E, zinc, hydroxyacids and glycyrrhetinic acid and a complex of glycyrrhetinic acid with phospholipids.

9. The composition according to claim 6, wherein said composition is a cosmetic composition for retarding skin aging.

10. A composition comprising:
    0.1-2.5% phospholipid complexes of standardized extract of *Vitis vinifera*;
    0.1-2.5% phospholipid complexes of standardized Extract of *Centella asiatica*;
    at least one of a pharmaceutically acceptable carrier and a pharmaceutically acceptable excipient and
    wherein said extracts are of vegetable origin.

* * * * *